(12) United States Patent
Ette et al.

(10) Patent No.: US 12,315,359 B2
(45) Date of Patent: May 27, 2025

(54) METHOD FOR DETERMINING THE POSITION AND VITAL PARAMETERS OF AN OCCUPANT OF A TRANSPORTATION VEHICLE AND TRANSPORTATION VEHICLE

(71) Applicant: VOLKSWAGEN AKTIENGESELLSCHAFT, Wolfsburg (DE)

(72) Inventors: Bernd Ette, Wolfsburg (DE); Patrick Sacher, Brome (DE)

(73) Assignee: VOLKSWAGEN AKTIENGESELLSCHAFT (DE)

( * ) Notice: Subject to any disclaimer, the term of this patent is extended or adjusted under 35 U.S.C. 154(b) by 154 days.

(21) Appl. No.: 18/447,345

(22) Filed: Aug. 10, 2023

(65) Prior Publication Data
US 2024/0054885 A1 Feb. 15, 2024

(30) Foreign Application Priority Data
Aug. 15, 2022 (DE) .................... 10 2022 208 460.8

(51) Int. Cl.
*B60Q 1/00* (2006.01)
*A61B 5/00* (2006.01)
(Continued)

(52) U.S. Cl.
CPC ............. *G08B 27/001* (2013.01); *A61B 5/05* (2013.01); *A61B 5/6893* (2013.01);
(Continued)

(58) Field of Classification Search
CPC ...... G08B 27/001; G08B 21/22; G08B 25/10; A61B 5/05; A61B 5/6893; A61B 2503/22; A61B 5/002; A61B 5/0507; A61B 5/18; B60N 2/0024; B60N 2/002; G01S 13/003; G01S 13/0209; G01S 7/006; G01S 7/41; H04B 2201/71632; H04B 1/3822; G07C 5/008; G07C 5/085; B60R 16/0231; G01C 21/16
(Continued)

(56) References Cited

U.S. PATENT DOCUMENTS 5,802,479 A * 9/1998 Kithil ................... B60N 2/0029
257/295
10,106,156 B1 * 10/2018 Nave ................. B60W 50/0098
(Continued)

FOREIGN PATENT DOCUMENTS

CN 113993100 A 1/2022
DE 102021206343 A1 12/2021
(Continued)

*Primary Examiner* — Anh V La
(74) *Attorney, Agent, or Firm* — BARNES & THORNBURG LLP (57) ABSTRACT

A method for determining the position and vital signs of an occupant of a transportation vehicle and a transportation vehicle having a radio system and a control unit connected to the radio system. The method is based on channel impulse response (CIR) measurements and is performed using at least two UWB antennas during the operation of the transportation vehicle to determine a position and a vital sign of one or more occupants of the transportation vehicle.

14 Claims, 3 Drawing Sheets

(51) Int. Cl.
    *A61B 5/05*          (2021.01)
    *B60N 2/00*         (2006.01)
    *G01S 13/00*        (2006.01)
    *G01S 13/02*        (2006.01)
    *G08B 27/00*       (2006.01)

(52) U.S. Cl.
    CPC .......... *B60N 2/0024* (2023.08); *G01S 13/003* (2013.01); *G01S 13/0209* (2013.01); *A61B 2503/22* (2013.01); *H04B 2201/71632* (2013.01)

(58) Field of Classification Search
    USPC .................. 340/436, 573.1, 435, 439, 425.5
    See application file for complete search history.

(56) References Cited

U.S. PATENT DOCUMENTS

| | | |
|---|---|---|
| 11,277,166 B2 | 3/2022 | Zeng et al. |
| 2003/0184065 A1 | 10/2003 | Breed et al. |
| 2016/0275790 A1 | 9/2016 | Kang et al. |
| 2019/0213429 A1* | 7/2019 | Sicconi .................. G06F 3/012 |
| 2020/0348406 A1 | 11/2020 | Jain et al. |
| 2022/0030408 A1 | 1/2022 | Zhang et al. |
| 2022/0075051 A1 | 3/2022 | Woo et al. |
| 2022/0091246 A1 | 3/2022 | Blomerius et al. |

FOREIGN PATENT DOCUMENTS

| | | |
|---|---|---|
| DE | 102020124444 A1 | 3/2022 |
| DE | 102020215852 A1 | 6/2022 |
| KR | 20200107639 A | 9/2020 |
| WO | 2021220190 A1 | 11/2021 |

\* cited by examiner

METHOD FOR DETERMINING THE POSITION AND VITAL PARAMETERS OF AN OCCUPANT OF A TRANSPORTATION VEHICLE AND TRANSPORTATION VEHICLE

PRIORITY CLAIM

This patent application claims priority to German Patent Application No. 10 2022 208 460.8, filed 15 Aug. 2022, the disclosure of which is incorporated herein by reference in its entirety.

SUMMARY

Illustrative embodiments relate to a method for determining the position and vital signs of an occupant of a transportation vehicle and a transportation vehicle having a radio system and a control unit connected to the radio system which is set up to perform the method using the radio system.

BRIEF DESCRIPTION OF THE DRAWINGS

Disclosed embodiments are explained in further detail below with reference to the drawings, in which.

DETAILED DESCRIPTION

The safety of occupants in transportation vehicles has long been the subject of modern development. Modern transportation vehicles contain a variety of safety systems intended to reduce the occurrence of accidents or their consequences. A classic example is an airbag. The airbag is activated by seat-resolved information from pressure sensors in the transportation vehicle seats and sensor values detected by inertial sensors installed in the transportation vehicle to protect the occupant from serious physical damage in the event of an accident as far as possible.

However, airbags can also deploy unintentionally. For example, it is difficult to distinguish between an object in the seat and a seated occupant based on the pressure sensor values alone. Therefore, it is obvious that there is a need for interior sensors that can distinguish an occupant from an object and can determine the position of the occupant as accurately as possible in the transportation vehicle to provide the safety systems of the transportation vehicle with the most precise basis possible to fulfil their intended purpose.

In the document WO 2021220190 A1, a method and a system for monitoring a transportation vehicle cabin are proposed, which propose a radar sensor array system in the headliner of the transportation vehicle that detects reflected signals from occupants in the transportation vehicle. Data analysis is used to determine the size of the occupant, his position, his movements and his vital signs. With just a single sensor arrangement, it is possible to carry out multi-functional monitoring of the transportation vehicle cabin and replace a plurality of sensors that would otherwise be required for this purpose.

Document DE 10 2020 124 444 A1 refers to a method and a monitoring device for monitoring an interior and/or exterior of a transportation vehicle. For this purpose, electromagnetic radiation is first transmitted into the interior and/or exterior and the electromagnetic radiation reflected on an object is received to derive from it information about a state of the object.

Further examples of position determination using electromagnetic radiation are described in documents DE 10 2021 206 343 A1 and DE 10 2020 215 852 A1.

Disclosed embodiments develop an alternative method for determining a position and a vital sign of a vehicle occupant.

This is achieved by a method for determining the position and vital signs of an occupant of a transportation vehicle and a transportation vehicle.

A first exemplary embodiment concerns a method for determining the position and vital signs of an occupant of a transportation vehicle. The transportation vehicle contains a radio system with a transceiver, with a first ultra-wide-band (UWB) antenna and with a second UWB antenna and a control unit connected to the radio system. The first UWB antenna and the second UWB antenna are set up to transmit and receive UWB pulses. The control unit is set up to actuate the radio system to carry out a channel impulse response (CIR) based method using the first UWB antenna and the second UWB antenna during the operation of the transportation vehicle and to determine the position and vital signs of the occupant based on a result of the CIR measurements. Vital signs are measurements that reflect basic functions of the human body and can be measured to check the vital functions. These include, for example, heart rate, blood pressure, body temperature and/or respiratory rate. Operation of the transportation vehicle means while driving the transportation vehicle and/or when the ignition of the transportation vehicle is switched on.

In particular, the transceiver is designed to transmit and receive signals in very wide frequency ranges, in particular, in a frequency range from 3.1 GHz to 10.6 GHz, optionally in a frequency range from 3.5 GHz to 9 GHz, optionally in a frequency range from 6 GHz to 8.5 GHz. The transmission power of the UWB pulses is low. The bandwidth of the UWB signal is at least 500 MHz and the UWB transceiver may be designed to transmit signals with a transmission power between 0.5 mW/−41.3 dBm/MHz. Furthermore, the transceiver may be designed according to the IEEE 802.15.4 standard (especially the sections on the UWB PHY layer) and optionally according to the IEEE 802.15.4z standard. Due to the spread of signals over such wide frequency ranges, UWB signals only minimally interfere with other radio signals.

Due to the strongly temporally localized UWB pulses, it is possible to extract information about the propagation path of the UWB pulses from received UWB pulses with their impulse response resulting from the influence of the surroundings on the transmitted UWB pulse. Environmental influences are based on physical phenomena that deflect the UWB pulse from its geometrically prescribed path, such as refraction, diffraction, reflection or damping. It is obvious that the propagation times of the signals or signal packets differ along different propagation paths and change depending on the presence or absence of objects in or near the propagation paths. The pulse shape of the signals or signal packets is also influenced depending on the presence or absence of objects in or near the propagation paths. Thus, the presence or absence of objects in or near the propagation paths can be inferred based on the measurement of signals or signal packets transmitted along these propagation paths.

Using only (at least) two UWB antennas, it is possible to scan the surroundings in a spatially resolved manner by CIR measurements. By multiple UWB pulse transmissions by one of the antennas and on the basis of the impulse responses received by the other antenna, changes in the surroundings—for example, a new object in the area to be scanned—can be revealed in a spatially resolved and time-resolved manner by comparing the time-shifted impulse responses. In this way, the detection of an object entering the area to be scanned is reliably possible. In particular, a particularly favored constant and/or repetitive scanning of the surroundings by OR measurements allows appropriate monitoring of the area to be scanned.

The CIR measurements include, for example, sending predefined signals or signal packets (so-called telegrams) between the (at least) two UWB antennas. In addition to a direct propagation path of the signal or the signal packets between the UWB antennas, there are a plurality of other propagation paths, which include, for example, reflections from objects from the interior or exterior of the transportation vehicle. Based on a sufficient number and/or a beneficial arrangement of the UWB antennas, these propagation paths allow coverage of large parts of a space, for example, a transportation vehicle interior or a transportation vehicle exterior. Of course, the OR measurements can be carried out between a large number of UWB antennas to scan appropriate areas, in particular, an interior of a transportation vehicle, depending on the arrangement of the UWB antennas.

The UWB antennas are arranged in such a way that one or more occupants in the transportation vehicle can be detected with seat accuracy or resolution. In particular, the seat occupancy of the transportation vehicle is detected during transportation vehicle operation. In addition, the CIR measurements can be used to resolve movements of the occupant(s), in particular, the chest movement of breathing by the occupant(s). Optionally, the two UWB antennas are located in doors, optionally in opposite doors, of the transportation vehicle. For example, the first UWB antenna may be located in the driver's door and the second UWB antenna may be located in the passenger door of the transportation vehicle. This allows the two front seats in a transportation vehicle to be monitored by CIR measurements. Of course, the UWB antennas can be arranged similarly or additional UWB antennas can be arranged in the two opposite rear doors of the transportation vehicle to monitor the rear seats. However, it is also possible to arrange the UWB antennas in any other way. Preference is given to a plurality of UWB antennas. This has the benefit that a plurality of occupants, their position and vital signs can be detected and monitored based on the CIR measurements. Furthermore, UWB antennas already installed in the transportation vehicle can be used for the disclosed method. Modern transportation vehicles sometimes have UWB antennas, which are installed in the transportation vehicle for keyless entry. As a result, the already installed UWB antennas will be used multifunctionally and costs will be saved. Furthermore, the additional use of already installed UWB antennas has the benefit that (partially) redundant antennas are available. Especially in an accident scenario, individual UWB antennas can be defective, but can be supplemented by redundant antennas. In this respect, the CIR measurements can still be carried out despite partially defective UWB antennas.

The determined position and movement data and the determined vital signs of the occupant may be stored in a memory unit of the transportation vehicle. By storing the position and movement data and the determined vital signs of the occupant, occupant-specific profiles can be created, which can be used in future situations to be able to make an individual and thus better decision in individual cases.

It is also provided that an accident involving the transportation vehicle will be detected. After the (detected) accident, the radio system is actuated again to carry out the method based on CIR measurements again using the first UWB antenna and the second UWB antenna. The position and vital signs of the occupant are determined again based on a result of the new OR measurements. Based on the changes in the position and vital signs of the occupant between before and after the accident, information about the effects of the accident on occupants can be derived. Knowledge of the number, position, state of health (vital signs), height (adult, child, baby) of the occupant or occupants can make it much easier for approaching rescue teams to rescue and recover the occupant or occupants and thus reduce the consequences of the accident. Of course, even after the accident, a large number of CIR measurements, in particular, as many as possible or necessary, can be carried out until, for example, no occupant is detected in the transportation vehicle.

Optionally, the determined position and movement data and the determined vital signs of the occupant or occupants are stored in the memory unit of the transportation vehicle after the accident. Optionally, an emergency mode of the transportation vehicle is activated after an accident. In the emergency mode, the transportation vehicle is set up to allow access to predetermined transportation vehicle functions from the outside and to output appropriate signals to the transportation vehicle components to carry out the predetermined transportation vehicle functions. For example, actuators can be actuated to control the unlocking of the central locking system or the opening of doors or windows. These actuators are usually only accessible from the interior of the transportation vehicle and are therefore all the more difficult for the rescue teams to operate to free occupants from the transportation vehicle. Optionally, operation of the actuators is possible in the emergency mode regardless of the transportation vehicle ignition status.

Optionally, seat-resolved detection of the occupant or occupants of the transportation vehicle takes place based on the determined position of the occupant or occupants before and after the accident. For example, the seat occupancy of the driver's seat, the front passenger seat and/or the rear seats can be used for this purpose. The information about the assignment of occupants to individual seats makes it easier for rescue teams to carry out appropriate rescue operations to free the occupant or occupants. For example, forcible access to the transportation vehicle can take place via a window pane or a transportation vehicle door where no occupant has been determined to reduce the risk of injury when rescuing the occupants.

It is also optional to compare the determined position and/or the determined vital signs of the occupant before the accident with the determined position and/or the determined vital signs of the occupant after the accident. As a result of this it can be beneficially determined whether and how an occupant has changed his or her position as a result of the accident, in particular, whether an occupant was thrown out of the transportation vehicle as a result of the accident and the rescue teams should therefore search for another occupant outside the transportation vehicle. Furthermore, detecting a living being and state of health on the basis of the vital signs may take place before and after the accident. In this way, it is possible to check individually for each occupant in which standard range his or her vital signs lie and whether the vital signs determined after the accident deviate from the standard range and therefore indicate a deteriorated state of health. In combination with the determined vital signs and the determined positions of the occupant(s), a rescue sequence for the occupants can be determined to free seriously injured persons before less injured occupants. Furthermore, it is optional to detect the equipment of the transportation vehicle to be able to provide this information to the rescue teams.

It is also optional to actuate the radio system based on a result of the comparison to transmit an emergency signal into the surroundings of the transportation vehicle. The emergency signal contains the determined positions and/or the determined vital signs of the occupant before and after the accident. In particular, the emergency signal also contains information about the equipment of the transportation vehicle. By transmitting the emergency signal by the radio system, other transportation vehicles or rescue facilities in the vicinity of the transportation vehicle can be informed about the emergency situation and detailed information about the occupants and the transportation vehicle to initiate a rescue operation.

Also optionally, the first UWB antenna and the second UWB antenna are further set up to transmit and receive BLUETOOTH® radio signals, and the radio system is actuated to transmit the emergency signal as a UWB radio signal and/or a BLUETOOTH® radio signal using the first UWB antenna and/or second antenna. BLUETOOTH® communication may take place in the well-known frequency band between 2.402 GHz and 2.480 GHz. BLUETOOTH® low energy wireless technology may be provided. Compared to known solutions, this uses a communication technology that can be made available directly in situ by the transportation vehicle without an active WLAN, GPS or LTE function. After an accident, the known solutions do not guarantee that the emergency signal could be transmitted to a control center in a timely manner. Technical problems of the communication systems of the transportation vehicle cannot be ruled out after an accident. The quality and availability of network connections cannot be reliably assessed either. Accordingly, in these cases too, the emergency signal can at least be received by mobile devices of persons or the rescue team in the surroundings of the transportation vehicle. Optionally, the antennas are actuated to transmit the emergency signals in a staggered manner to save energy and increase the transmission time. For example, the emergency signal is transmitted every ten seconds.

Also preferably, the emergency signal may contain general information about the transportation vehicle. For example, this information may concern the circumstance of whether it is an electric car or a gasoline-powered car, which may pose an increased risk of fire. In addition, the general information may include the location and deployment of the airbags of the transportation vehicle or the points on the body of the transportation vehicle where shears can be safely used to open the transportation vehicle.

Also, the radio system may contain an NFC antenna for transmitting the emergency signal, wherein the information required for the emergency signal is stored in an NFC memory after an accident. Optionally, the wireless system includes the NFC memory. Optionally, the NFC antenna is an NFC reader or NFC tag. An NFC reader is an active component in NFC transmissions. It is able to read and write NFC tags and can communicate directly with other devices. An NFC tag, on the other hand, is dependent on a power supply from another NFC device and is able to transmit information from the NFC memory by NFC based on the power supply of the other NFC device. Rescue teams can use an NFC-enabled device to receive the emergency signal and the determined positions and vital signs of the occupant or occupants via the NFC antenna. In the case of the NFC tag, this works even after the power supply of the transportation vehicle has failed.

In a further disclosed embodiment, it is provided that the radio system is actuated for transmitting UWB pulses and receiving impulse responses using at least one of the two UWB antennas and that the position and/or vital signs of the occupant or occupants are further determined based on a result of the received impulse responses. In contrast to the CIR measurements, with the method with the received impulse responses the same UWB antenna that transmits the UWB signal also receives the impulse response. In this respect, an echo of the scanned surroundings is received. This echo usually represents a plurality of time-resolved echo signals, which are reflected in the impulse response depending on the distance between these objects and/or people and the transceiver. By comparing the echo signals using time shifted UWB pulses and their received impulse responses, conclusions can be drawn about changes in the location of the objects and/or persons in relation to the transceiver. The vital signs can be determined from the changes in location. The echo signals may be determined on the basis of amplitude and/or phase information and compared with each other. As a result, it is possible to scan the interior of the transportation vehicle with spatial and temporal resolution using at least one antenna. Of course, the UWB antennas or other UWB antennas installed in the transportation vehicle can also carry out the method of received impulse responses to scan the surroundings and/or the interior of the transportation vehicle from different angles in a spatially resolved and time-resolved manner.

The farther away an object is from the transceiver, the later the echo signal associated with the object is received by the transceiver. For example, a range of the transceiver can be limited by interrupting the reception of the impulse response after a time corresponding to the desired range and/or by transmitting a new UWB pulse. During the time in which the UWB pulse is transmitted via the transceiver, it is not possible to receive the impulse response by the transceiver used for transmitting.

The method which is based on the received impulse responses can use existing UWB antennas of the transportation vehicle, which are usually used for the detection of the surroundings of the transportation vehicle. This is because these UWB antennas are usually not used for transmitting UWB signals into the interior of the transportation vehicle and are therefore available. In this respect, the existing UWB antennas can be used multifunctionally and costs can be saved. Furthermore, UWB antennas can be defective after an accident, so it is beneficial that this procedure can be carried out by only one UWB antenna. Consequently, in the event of an accident, it may be provided that the radio system may be actuated using at least one of the two antennas to carry out the method which is based on receiving impulse responses of transmitted UWB pulses for determining the position and vital signs of the occupant after the accident.

Another exemplary embodiment involves a transportation vehicle with a radio system and a control unit connected to the radio system. The radio system contains a transceiver with a first UWB antenna and a second UWB antenna. The control unit is set up to carry out the foregoing. The features described by the method and their benefits can be realized analogously with the transportation vehicle and can therefore be combined with each other as desired.

In an exemplary embodiment, it is envisaged that the transportation vehicle further has a sensor unit which is set up together with the control unit to detect an accident of the transportation vehicle. The sensor unit may contain an inertial sensor, a receiver of an airbag deployment signal and/or a camera. The inertial sensor may contain an accelerometer, a shock sensor and/or a rollover sensor. The control unit may be set up to detect an accident of the transportation vehicle from the detected values of the inertial sensor, from the airbag deployment signal receiver and/or from the camera images generated.

The aforementioned control unit of the transportation vehicle may be implemented with electrical or electronic parts or components (hardware) or by firmware (ASIC). In addition or alternatively, the functionality of the control unit is realized when running a suitable program (software). Also, the control unit may be realized by a combination of hardware, firmware and/or software. For example, individual components of the control unit are designed to provide individual functionalities as a separate integrated circuit or are arranged on a common integrated circuit.

The individual components of the control unit may also be designed as one or more processes running on one or more processors in one or more electronic computing devices and are generated when one or more computer programs are executed. The computing devices may be designed to work together with other components, such as a central locking system, a motor controller, etc., to realize the functionalities described herein. The instructions of the computer programs may be stored in a memory, such as a RAM element. However, the computer programs may also be stored in a non-volatile memory medium, such as a CD-ROM, flash memory or the like.

It is also apparent to those skilled in the art that the functionalities of multiple computing units (data processing devices) may be combined, or may be combined in a single device, or that the functionality may be distributed from a particular computing device to a plurality of devices to realize the functionality of the control unit.

A further exemplary embodiment relates to a computer program containing instructions which, when executed by a computer, such as a control device of a transportation vehicle having a radio system having a transceiver having a first UWB antenna and a second UWB antenna, cause the latter to carry out the disclosed method, in particular, a method for determining the position and vital signs of an occupant of a transportation vehicle.

The various embodiments mentioned in this application can be combined with each other unless otherwise stated in the individual case.

Figure 1:
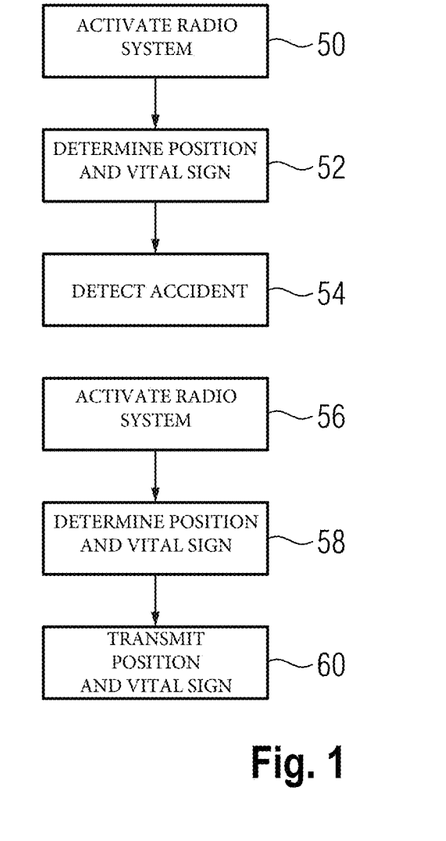
FIG. 1 schematically shows a representation of a disclosed method according to an exemplary embodiment.
Figure 2:
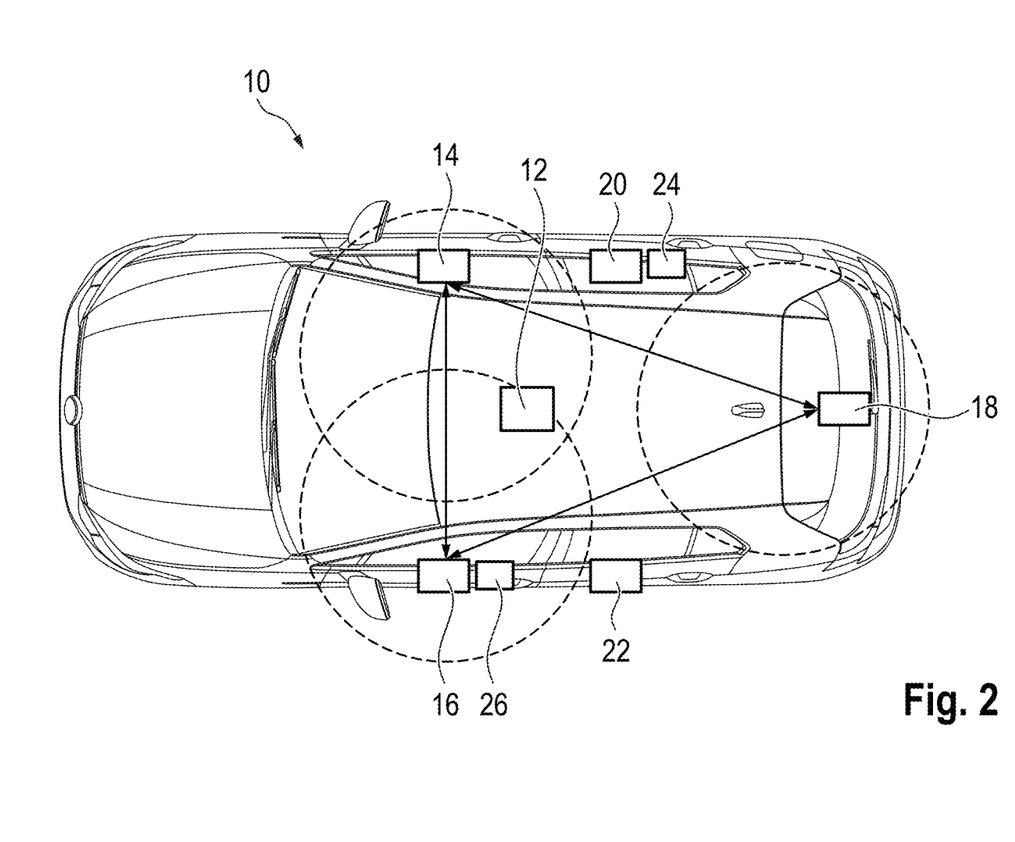
FIG. 2 schematically shows a representation of a transportation vehicle according to an exemplary embodiment with five UWB antennas.
Figure 3:
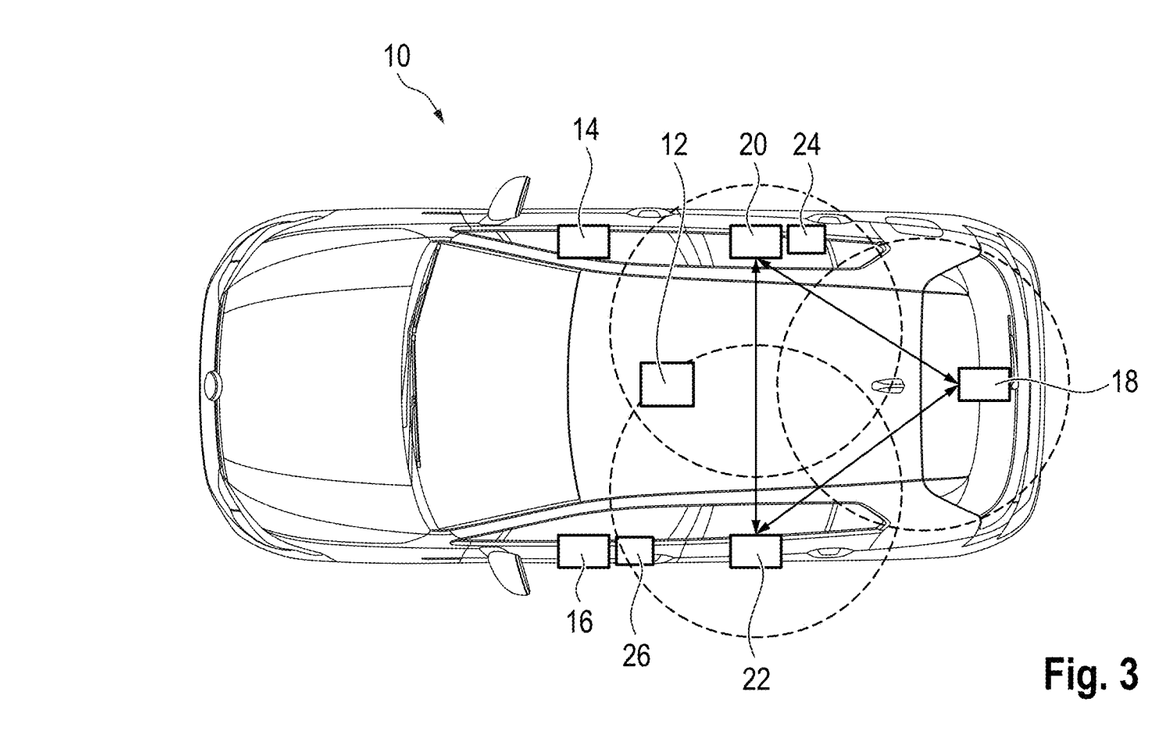
FIG. 3 shows a schematic diagram of a transportation vehicle with five UWB antennas according to a further exemplary embodiment.

FIG. 1 shows a schematic representation of a method according to an exemplary embodiment. The method is suitable for determining the position and vital signs of an occupant of a transportation vehicle 10. With reference to FIGS. 2 and 3, the transportation vehicle 10 is described in more detail on the basis of two exemplary embodiments.

The transportation vehicle 10 contains a radio system with a transceiver having at least a first UWB antenna 14 and a second UWB antenna 16 and a control unit 12 connected to the radio system. In particular, the control unit 12 is set up to carry out the method described in FIG. 1. FIGS. 2 and 3 show an exemplary transportation vehicle 10 with a radio system, a transceiver and first to fifth UWB antennas 14, 16, 18, 20, 22. The five UWB antennas 14, 16, 18, 20, 22 are distributed over the five doors of the transportation vehicle 10. Accordingly, the first UWB antenna 14 is located in the passenger door, the second UWB antenna 16 in the driver's door, the third UWB antenna 18 in the tailgate, the fourth UWB antenna 20 in the door behind the passenger door and the fifth UWB antenna 22 in the door behind the driver's door. The number and arrangement of the UWB antennas 14, 16, 18, 20, 22 is only of an exemplary nature, which should serve the purpose of a better understanding. The disclosure is not limited to the array and number of UWB antennas 14, 16, 18, 20, 22 shown.

In a first operation at 50 of the method, the radio system for carrying out a method based on CIR measurements using the first UWB antenna 14 and the second UWB antenna 16 is activated during the operation of the transportation vehicle 10. With reference to FIG. 2, it is shown that the radio system for carrying out the method based on CIR measurements using the first UWB antenna 14, the second UWB antenna 16 and the third UWB antenna 18 is activated during the operation of the transportation vehicle 10. With reference to FIG. 3, it is illustrated that the radio system for carrying out the method based on CIR measurements using the fourth UWB antenna 20, the fifth UWB antenna 22 and the third UWB antenna 18 is activated during the operation of the transportation vehicle 10. Obviously, CIR measurements can also take place between other, especially all, UWB antennas 14, 16, 18, 20, 22 to obtain information about occupants and objects along the propagation path between the respective UWB antennas 14, 16, 18, 20, 22.

In a second operation at 52 of the method, a position and a vital sign of an occupant of the transportation vehicle 10 are determined based on a result of the CIR measurements. In this operation of the method, a position and a vital sign of a plurality, in particular, all, of the occupants of the transportation vehicle 10 can also be determined based on a result of the CIR measurements. The determined position and the determined vital sign are stored in a memory unit of the transportation vehicle 10.

In a third operation at 54 of the method, an accident of the transportation vehicle 10 is detected. This can take place using a sensor unit of the transportation vehicle 10 and the control unit 12. For this purpose, the sensor unit contains a shock sensor, the detected values of which are transferred to the control unit 12, wherein the control unit 12 is set up to distinguish whether or not an accident situation of the transportation vehicle 10 exists based on the detected parameter values of the shock sensor. However, the sensor unit may also contain other sensors for detecting an accident of the transportation vehicle 10 and the control unit 12 may be set up accordingly to decide whether or not an accident has occurred based on the values detected by the other sensors.

In a fourth operation at 56 of the method, the radio system is activated to carry out the CR-based method again using the first UWB antenna 14 and the second UWB antenna 16 after the accident. Also in this operation of the method, the CIR measurements can take place in any combination between the UWB antennas 14, 16, 18, 20, 22.

In a fifth operation at 58 of the method, the position and vital signs of the occupant are determined based on a result of the new OR measurements. The newly determined position and the newly determined vital sign are also stored in the memory unit of the transportation vehicle 10. The fourth and fifth operations at 56, 58 of the method can be repeated as often as desired, in particular, periodically, to monitor the interior of the transportation vehicle.

In a sixth operation at 60 of the method, the determined positions and the determined vital signs of the occupant are transmitted to the surroundings of the transportation vehicle as an emergency signal using the radio system. The fact that the emergency signal contains targeted information about the position and vital signs before and after the accident allows rescue workers to carry out a targeted and thus improved rescue measure for the occupant or occupants of the transportation vehicle 10 on the basis of the additional information in the emergency signal. As a result, lives can be saved better and the consequences of the accident can be reduced.

As shown in FIG. 2 as an example, CIR measurements between the first and second UWB antennas 14, 16 can be used to detect one or more occupants in the front seats of the transportation vehicle 10 with seat resolution (see arrow between UWB antennas 14 and 16). However, to detect occupants in other seats in the interior of transportation vehicle 10, the other UWB antennas 18, 20, 22 are provided. The arrows between the UWB antennas 14 and 18 as well as 16 and 18 illustrate that by corresponding CIR measurements between these UWB antennas 14, 16, 18, occupants in the rear seats of transportation vehicle 10 can also be detected with seat resolution. It is obvious that the aforementioned benefits are also achieved between the UWB antennas 14 and 22 and 16 and 24 or accordingly—as explicitly shown in FIG. 3—between the UWB antennas 18, 20, 22 in the rear part of the transportation vehicle for the rear seats.

FIGS. 2 and 3 show another exemplary embodiment according to which the UWB antennas 14, 16, 18, 20, 22 can be used not only for mutual CIR measurements. Rather, each UWB antenna 14, 16, 18, 20, 22 can transmit UWB pulses on its own and can receive the echo signals of the interior of the transportation vehicle based on received impulse responses. From these received impulse responses, the position and vital signs of the occupant or occupants can also be determined. As an example, a range of the method of the received impulse responses of each UWB antenna 14, 16, 18, 20, 22 is shown as a dashed circle. However, the circles, which have a radius of about one meter, are not limited to this dimension. Rather, this method can also be used to achieve ranges of up to 10 meters from the respective UWB antenna 14, 16, 18, 20, 22. In this respect, the method presented here can also be applied to transportation vehicles 10 with larger transportation vehicle interiors such as vans, buses, caravans and so on. FIGS. 2 and 3 illustrate that the entire interior of the transportation vehicle 10 can be scanned and thus monitored with the five UWB antennas 14, 16, 18, 20, 22 selected as an example. Consequently, the position and vital signs of each occupant of the transportation vehicle 10 can be determined.

FIGS. 2 and 3 also illustrate that the transceiver of the radio system also has a first and a second NFC antenna 24, 26. The first NFC antenna 24 is arranged in the driver's door, while the second NFC antenna 26 is installed in the door behind the passenger door. The NFC antennas 24, 26 can be used to transmit the determined positions and the determined vital signs of the occupant or occupants of the transportation vehicle 10 before and after the accident to emergency services by NFC. This exemplary positioning has the benefit that the transportation vehicle 10 enables communication via NFC from two opposite sides, so that in most accident situations communication can be established with at least one of the two NFC antennas 24, 26. The determined positions and vital signs of the occupant or occupants of the transportation vehicle 10 before and after the accident are stored in a memory of the respective NFC antenna 24, 26. Rescue workers can access this information by NFC communication and carry out individually suitable rescue measures. As an example only, the first NFC antenna 24 is designed as an NFC reader and the second NFC antenna 26 as an NFC tag. This has the benefit that even if the power supply of the transportation vehicle 10 fails, the information can be received by the emergency services via the second NFC antenna 26.

REFERENCE SIGN LIST 10 transportation vehicle
12 control unit
14 first UWB antenna
16 second UWB antenna
18 third UWB antenna
20 fourth UWB antenna
22 fifth UWB antenna
24 first NFC antenna
26 second NFC antenna
50 first operation of the method
52 second operation of the method
54 third operation of the method
56 fourth operation of the method
58 fifth operation of the method
60 sixth operation of the method

The invention claimed is:

1. A transportation vehicle comprising:
a radio system with a transceiver with a first Ultra-Wide-Band (UWB) antenna and a second UWB antenna; and
a control unit connected to the radio system, wherein the control unit is configured to control the radio system to determine a position and vital signs of an occupant of a transportation vehicle by actuation of the radio system based on channel impulse response measurements using the first UWB antenna and the second UWB antenna during the operation of the transportation vehicle by determination of the position and a vital sign of the occupant based on a result of the channel impulse response measurements,
wherein, following detection of an accident of the transportation vehicle, the control unit controls actuation of the radio system to re-perform the determination of the position and vital signs of the transportation vehicle occupant based on new channel impulse response measurements using the first UWB antenna and the second UWB antenna after the accident, and
wherein the control unit is further configured to determine whether the occupant was ejected from the vehicle as a result of the accident by comparing the detected position and/or the vital sign of the occupant before the accident with the determined position and/or the vital sign of the occupant after the accident.

2. The transportation vehicle of claim 1, wherein a seat-resolved detection of the occupant of the transportation vehicle takes place based on the determined position of the occupant before and after the accident.

3. The transportation vehicle of claim 1, wherein the radio system is actuated based on a result of a comparison to transmit an emergency signal into surroundings of the transportation vehicle, wherein the emergency signal contains the determined positions and/or the determined vital signs of the occupant before and after the detected accident.

4. The transportation vehicle of claim 3, wherein the first UWB antenna and the second UWB antenna transmit and receive BLUETOOTH® radio signals and the radio system is actuated to transmit the emergency signal as a UWB radio signal and/or a BLUETOOTH® radio signal using the first UWB antenna and/or second antenna.

5. The transportation vehicle of claim 3, wherein the emergency signal contains general information about the transportation vehicle.

6. The transportation vehicle of claim 3, wherein the radio system further contains a Near-Field-Communication (NFC) antenna for transmitting the emergency signal, wherein the information required for the emergency signal is stored in a memory after an accident.

7. The transportation vehicle of claim 1, wherein the control unit is further configured to control:
actuation of the radio system for transmitting UWB pulses and receipt of impulse responses using at least one of the two UWB antennas; and
determination of the position and/or the vital sign of the occupant based on a result of the received impulse responses.

8. A method for determining the position and vital signs of an occupant of a transportation vehicle, wherein the transportation vehicle has a radio system with a transceiver with a first Ultra-Wide-Band (UWB) antenna and with a second UWB antenna and a control unit connected to the radio system, the method comprising:
actuating the radio system based on channel impulse response measurements using the first UWB antenna and the second UWB antenna during the operation of the transportation vehicle;
determining the position and a vital sign of the occupant based on a result of the Channel Impulse Response (CIR) measurements;
following detection of an accident of the transportation vehicle, actuating the radio system to re-perform the actuation and determination of the position and the vital sign of the occupant based on new channel impulse response measurements using the first UWB antenna and the second UWB antenna after the accident; and
determining whether the occupant was ejected from the vehicle as a result of the accident by comparing the detected position and/or the vital sign of the occupant before the accident with the determined position and/or the vital sign of the occupant after the accident.

9. The method of claim 8, wherein a seat-resolved detection of the occupant of the transportation vehicle takes place based on the determined position of the occupant before and after the accident.

10. The method of claim 8, wherein the radio system is actuated based on a result of a comparison to transmit an emergency signal into surroundings of the transportation vehicle, wherein the emergency signal contains the determined positions and/or the determined vital signs of the occupant before and after the accident.

11. The method of claim 10, wherein the first UWB antenna and the second UWB antenna transmit and receive BLUETOOTH® radio signals and the radio system is actuated to transmit the emergency signal as a UWB radio signal and/or a BLUETOOTH® radio signal using the first UWB antenna and/or second antenna.

12. The method of claim 10, wherein the emergency signal contains general information about the transportation vehicle.

13. The method of claim 10, wherein the radio system further contains a Near-Field-Communication (NFC) antenna for transmitting the emergency signal, wherein the method further comprises storing information required for the emergency signal in a memory after an accident.

14. The method of claim 10, further comprising:
actuating the radio system for transmitting UWB pulses and receiving impulse responses using at least one of the two UWB antennas; and
determining the position and/or the vital sign of the occupant based on a result of the received impulse responses.

* * * * *